(12) United States Patent
Chen et al.

(10) Patent No.: US 9,464,046 B2
(45) Date of Patent: Oct. 11, 2016

(54) METHOD FOR PREPARING ORGANIC SELENIUM COMPOSITION

(71) Applicant: SHANGHAI AI QI ECOLOGICAL TECHNOLOGY CO., LTD., Shanghai (CN)

(72) Inventors: Gong Chen, Shanghai (CN); Kunyuan Song, Shanghai (CN)

(73) Assignee: Shanghai Ai Qi Ecological Technology Co. Ltd., Shanghai (CN)

( * ) Notice: Subject to any disclaimer, the term of this patent is extended or adjusted under 35 U.S.C. 154(b) by 0 days.

(21) Appl. No.: 14/004,160

(22) PCT Filed: Jul. 3, 2013

(86) PCT No.: PCT/CN2013/078728
§ 371 (c)(1),
(2) Date: Sep. 9, 2013

(87) PCT Pub. No.: WO2014/153893
PCT Pub. Date: Oct. 2, 2014

(65) Prior Publication Data
US 2016/0016902 A1   Jan. 21, 2016

(30) Foreign Application Priority Data
Mar. 25, 2013  (CN) .......................... 2013 1 0097463

(51) Int. Cl.
| | | |
|---|---|---|
| *C07D 265/36* | (2006.01) | |
| *C07D 311/56* | (2006.01) | |
| *C07D 493/04* | (2006.01) | |
| *C07C 391/00* | (2006.01) | |
| *C12P 39/00* | (2006.01) | |
| *C12P 9/00* | (2006.01) | |

(52) U.S. Cl.
CPC ............ *C07C 391/00* (2013.01); *C07D 265/36* (2013.01); *C07D 311/56* (2013.01); *C07D 493/04* (2013.01); *C12P 9/00* (2013.01); *C12P 39/00* (2013.01)

(58) Field of Classification Search
CPC   C07D 265/36; C07D 311/56; C07D 493/04; C07C 391/00
USPC .................................. 544/105; 549/401, 458
See application file for complete search history.

(56) References Cited

U.S. PATENT DOCUMENTS 4,166,820 A * 9/1979 Spallholz .............. C07C 391/00
                                                                    436/542

* cited by examiner

*Primary Examiner* — Kahsay Habte (57) ABSTRACT

A method for preparing selenium compounds, comprising following steps of: A. hydrolyzing lignin to obtain multiple-structural polyphenolic compounds; B. reacting the multiple-structural polyphenolic compounds with at least one kind of inorganic metal base to obtain multivalent phenolic hydroxyl carboxylate; and C. reacting the multivalent phenolic hydroxyl carboxylate with $SeO_2$ to obtain multivalent phenolic hydroxyl carboxylic acid selenium complex salts, wherein the multivalent phenolic hydroxyl carboxylic acid selenium complex salts are organic selenium composition. The multivalent phenolic hydroxyl carboxylic acid selenium complex salts have characteristics of over 20% selenium content and no toxicity, and have revolutionary effects in killing bacteria, virus and cancer cell, enhancing human immunity, removing oxygen free radicals and etc.

9 Claims, 2 Drawing Sheets a) hydrolyzing lignin to obtain multiple-structural polyphenolic compounds;

b) reacting the multiple-structural polyphenolic compounds with at least one kind of inorganic metal base to obtain multivalent phenolic hydroxyl carboxylate;

c) reacting the multivalent phenolic hydroxyl carboxylate with $SeO_2$ to obtain multivalent phenolic hydroxyl carboxylic acid selenium complex salts, wherein the multivalent phenolic hydroxyl carboxylic acid selenium complex salts are organic selenium composition.

Fig. 1

| No. | Ret.Time min | Peak Name | Height mAU | Area mAU*min | Rel.Area % | Amount | Type |
|---|---|---|---|---|---|---|---|
| 1 | 1.28 | n.a. | 16.989 | 5.779 | 35.31 | n.a. | BM |
| 2 | 1.93 | n.a. | 32.631 | 1.706 | 10.42 | n.a. | Mb |
| 3 | 2.15 | n.a. | 16.319 | 1.645 | 10.05 | n.a. | bMb |
| 4 | 2.45 | n.a. | 2.413 | 0.233 | 1.42 | n.a. | bMB* |
| 5 | 6.20 | n.a. | 0.913 | 0.231 | 1.41 | n.a. | BMB* |
| 6 | 7.17 | n.a. | 2.173 | 0.351 | 2.14 | n.a. | BMB |
| 7 | 8.52 | n.a. | 1.138 | 0.234 | 1.43 | n.a. | BMB |
| 8 | 9.23 | n.a. | 1.782 | 0.353 | 2.16 | n.a. | BMB |
| 9 | 9.73 | n.a. | 0.437 | 0.043 | 0.26 | n.a. | BM |
| 10 | 9.88 | n.a. | 0.867 | 0.111 | 0.68 | n.a. | Mb |
| 11 | 10.15 | n.a. | 5.195 | 0.577 | 3.52 | n.a. | bM |
| 12 | 10.40 | n.a. | 1.192 | 0.133 | 0.81 | n.a. | Mb |
| 13 | 10.78 | n.a. | 0.520 | 0.055 | 0.34 | n.a. | bMb |
| 14 | 10.97 | n.a. | 0.279 | 0.027 | 0.17 | n.a. | bMB |
| 15 | 11.33 | n.a. | 2.181 | 0.310 | 1.89 | n.a. | BMB* |
| 16 | 11.95 | n.a. | 0.399 | 0.046 | 0.28 | n.a. | BM * |
| 17 | 12.13 | n.a. | 0.622 | 0.086 | 0.52 | n.a. | MB* |
| 18 | 13.32 | n.a. | 0.441 | 0.056 | 0.34 | n.a. | BMB |
| 19 | 13.97 | n.a. | 1.086 | 0.197 | 1.21 | n.a. | BMB* |
| 20 | 14.80 | n.a. | 3.363 | 0.611 | 3.74 | n.a. | BMB |
| 21 | 16.02 | n.a. | 0.449 | 0.095 | 0.58 | n.a. | BMB* |
| 22 | 16.85 | n.a. | 1.916 | 0.304 | 1.86 | n.a. | BMB* |
| 23 | 17.58 | n.a. | 18.819 | 2.545 | 15.55 | n.a. | BMB* |
| 24 | 18.40 | n.a. | 0.756 | 0.096 | 0.58 | n.a. | BM * |
| 25 | 18.63 | n.a. | 0.239 | 0.025 | 0.15 | n.a. | Ru |
| 26 | 18.83 | n.a. | 3.323 | 0.516 | 3.15 | n.a. | MB* |
| Total: | | | 116.433 | 16.367 | 100.00 | 0.000 | |

METHOD FOR PREPARING ORGANIC SELENIUM COMPOSITION

CROSS REFERENCE OF RELATED APPLICATION

This is a U.S. National Stage under 35 U.S.C 371 of the International Application PCT/CN2013/078728, filed Jul. 3, 2013, which claims priority under 35 U.S.C. 119(a-d) to CN 201310097463.X, filed Mar. 25, 2013.

BACKGROUND OF THE PRESENT INVENTION

1. Field of Invention

The present invention mainly relates to a method for preparing a new type of organic selenium composition, and more particularly to a method for preparing multivalent phenolic hydroxyl carboxylic acid selenium complex salts.

2. Description of Related Arts

Selenium is an essential trace element of human metabolism. However, the uneven distribution of selenium element on the earth causes that over 40 countries and regions are deficient in selenium, and long-term residents thereof are more likely to be troubled with diseases such as cardio-cerebrovascular diseases, liver diseases, diabetes mellitus and cancers. Thus, the long-term residents thereof need selenium supplements. Due to high toxicity and indigestibility thereof, the inorganic selenium has been forbidden in some countries. With characteristics of low toxicity and high bioavailability, the organic selenium is the optimum selenium source. Therefore, the organic selenium has been a research focus. European and American professionals have already realized that in order to treat serious diseases, the organic selenium must be in an ultra high dose. However, organic selenium which is in an ultra high dose and nontoxic is not developed in the conventional art.

SUMMARY OF THE PRESENT INVENTION

A first object of the present invention is to provide a method for preparing a new type of organic selenium composition.

A second object of the present invention is to provide a new type of organic selenium composition, comprising multivalent phenolic hydroxyl carboxylic acid selenium complex salts.

A third object of the present invention is to provide multivalent phenolic hydroxyl carboxylic acid selenium complex salts with high selenium content and low toxicity.

Accordingly, in order to accomplish the above objects, the present invention provides a method for preparing an organic selenium composition, comprising following steps of:

a) hydrolyzing lignin to obtain multiple-structural polyphenolic compounds;

b) reacting the multiple-structural polyphenolic compounds with at least one kind of inorganic metal base to obtain multivalent phenolic hydroxyl carboxylate; and c) reacting the multivalent phenolic hydroxyl carboxylate with $SeO_2$ to obtain multivalent phenolic hydroxyl carboxylic acid selenium complex salts, wherein the multivalent phenolic hydroxyl carboxylic acid selenium complex salts are the organic selenium composition.

Beneficial effects of the present invention are as follows. The multivalent phenolic hydroxyl carboxylic acid selenium complex salts according to a preferred embodiment of the present invention have characteristics of over 20% selenium content and no toxicity, and have revolutionary effects in killing bacteria, virus and cancer cell, enhancing human immunity, removing oxygen free radicals and etc.

These and other objectives, features, and advantages of the present invention will become apparent from the following detailed description, the accompanying drawings, and the appended claims.

DETAILED DESCRIPTION OF THE PREFERRED EMBODIMENT

Figure 1:
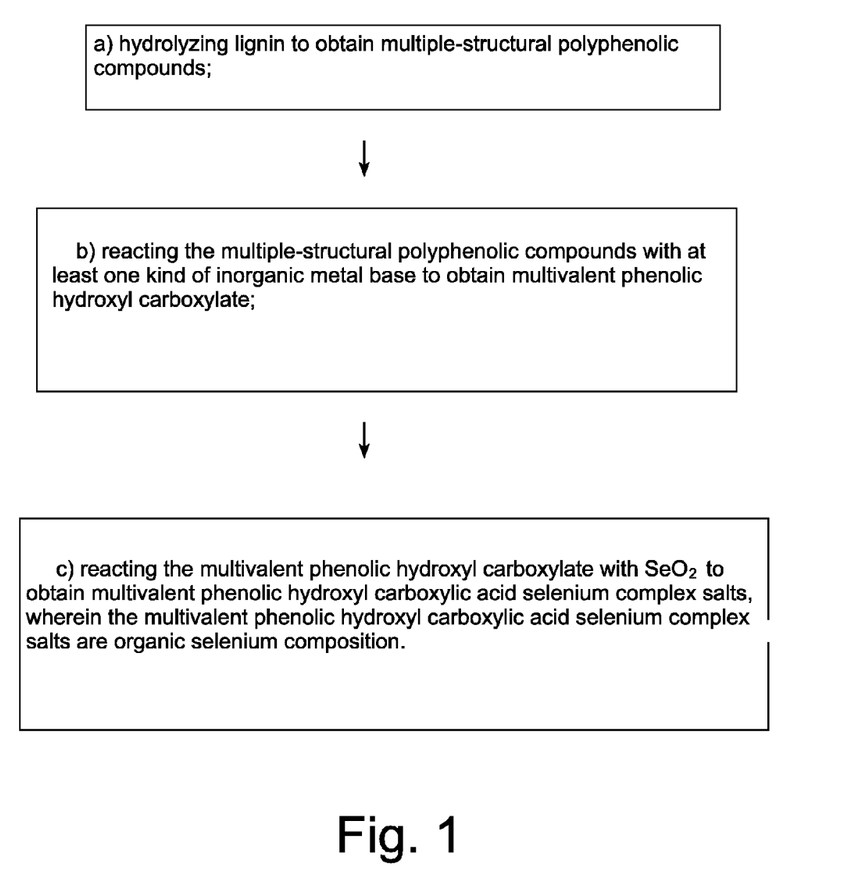
FIG. 1 is a flow chart of multivalent phenolic hydroxyl carboxylic acid selenium complex salts according to a preferred embodiment of the present invention.
Figure 2:
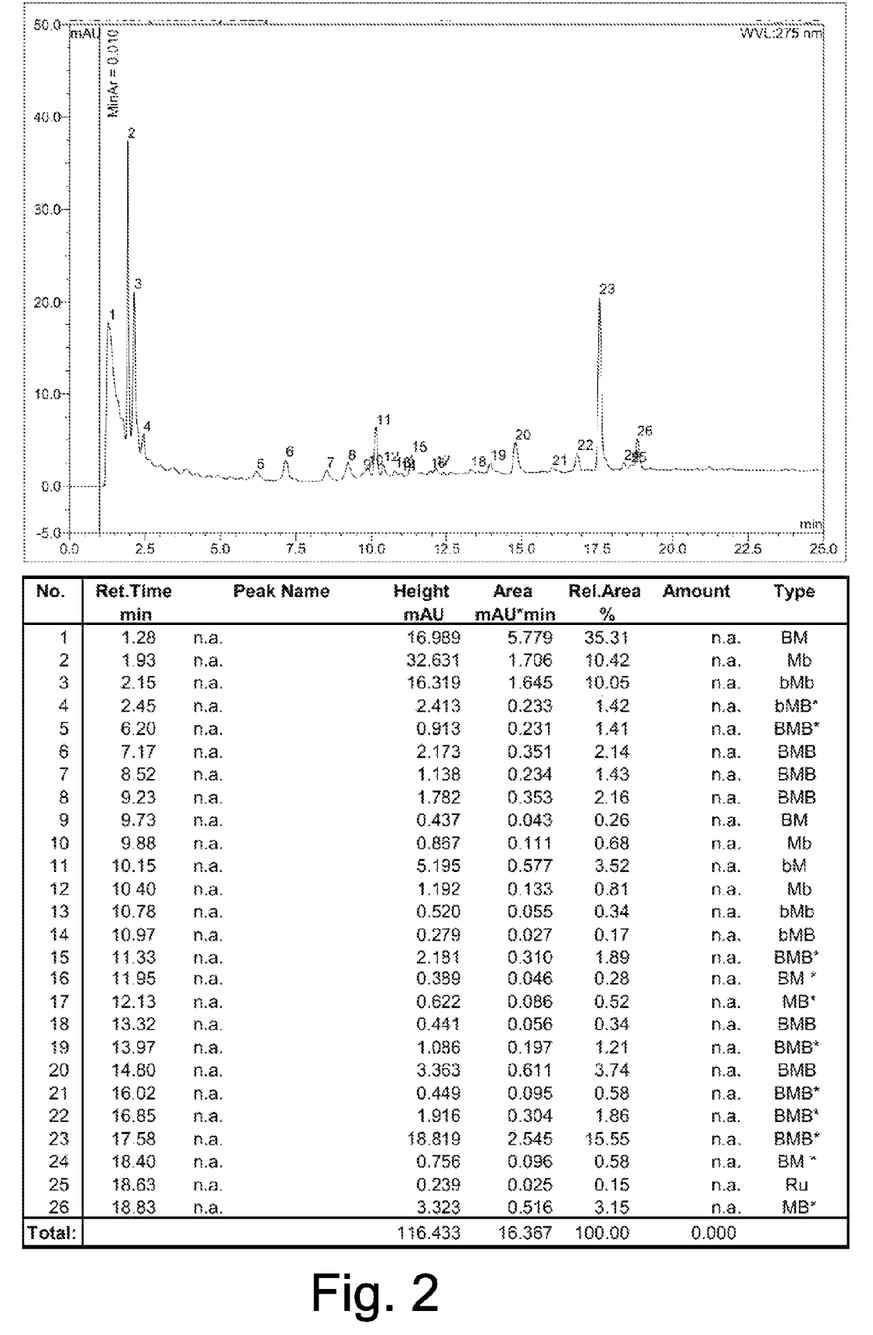
FIG. 2 is a high performance liquid chromatography diagram of multivalent phenolic hydroxyl carboxylic acid selenium complex salts according to a preferred embodiment 2 of the present invention.

Referring to FIG. 1 and FIG. 2 of the drawings, a method for preparing an organic selenium composition according to a preferred embodiment of the present invention is illustrated, comprising following steps of:

A. hydrolyzing lignin to obtain multiple-structural polyphenolic compounds;

B. reacting the multiple-structural polyphenolic compounds with at least one kind of inorganic metal base to obtain multivalent phenolic hydroxyl carboxylate; and C. reacting the multivalent phenolic hydroxyl carboxylate with $SeO_2$ to obtain multivalent phenolic hydroxyl carboxylic acid selenium complex salts, wherein the multivalent phenolic hydroxyl carboxylic acid selenium complex salts are the organic selenium composition.

According to a preferred embodiment of the present invention, specific process of the step A comprises following steps of:

adding 0.5~4.0% urea into lignosulfonate-water solution having 5~30% solid formation for serving as growth medium (pH=4.5~6.5), wherein the lignosulfonate-water solution is extracted from depickling paper pulp by sulphuric acid; and inoculating the growth medium with 0.5~10% mixed strains comprising: candida tropicalis, pseudomonas, candida utilis and strains of effective microorganisms from Japan and fermenting to obtain the multiple-structural polyphenolic compounds, wherein a fermentation temperature thereof is 20~40° C.

Preferably, the step A comprises specific following process of:

adding 2.0% of the urea into the lignosulfonate-water solution having 20% of the solid formation for serving as the growth medium (pH=6.0), wherein the lignosulfonate-water solution is extracted from the depickling paper pulp by the sulphuric acid; and inoculating the growth medium with 2% of the mixed strains comprising: the candida tropicalis, the pseudomonas, the candida utilis and the strains of effective microorganisms from Japan, and fermenting to obtain the multiple-structural polyphenolic compounds, wherein an inoculation ratio thereof is 1:2:2:2, the fermentation temperature thereof is 30° C., a fermentation time thereof is 72 h, and a content of the multiple-structural polyphenolic compounds is over 20%.

According to a preferred embodiment of the present invention, a material ratio in the step B is:

multiple-structural polyphenolic compounds: inorganic and metal base=1:0.1~0.8, wherein a reaction temperature thereof is 80° C.~200° C., and materials are mechanically stirred to be uniformly mixed while reacting.

According to a preferred embodiment of the present invention, a material ratio in the step C is:

multiple-structural polyphenolic compounds: $SeO_2$=1: 0.03~0.5, wherein a reaction temperature thereof is 80° C.~180° C., and materials are mechanically stirred to be uniformly mixed while reacting.

According to a preferred embodiment of the present invention, the inorganic and metal base is selected from the group consisting of potassium hydroxide, sodium hydroxide, calcium hydroxide, magnesium hydroxide, manganese hydroxide, lithium hydroxide and zinc hydroxide.

According to a preferred embodiment of the present invention, the multivalent phenolic hydroxyl carboxylate has the following active fragment:

wherein $R^+$ is at least one kind of alkali metal ion.

According to a preferred embodiment of the present invention, the multivalent phenolic hydroxyl carboxylate has the following active fragment:

According to a preferred embodiment of the present invention, the multiple-structural polyphenolic compounds appear to be slightly acidic, and a pH value thereof is 4.5~6.5. The multiple-structural polyphenolic compounds have good water-solubility, an average molecular weight thereof is 200~500, and elemental compositions thereof are as following: C: 38.00-44.00%, H: 2.20-4.29%, O: 40.00-45.00%, N: 2.00-4.00%, S: 3.00-5.00%.

Molecules of the multiple-structural polyphenolic compounds have aromatic rings or other heterocycles comprising pyrrole, furan and indole. The aromatic rings are connected by bridge bond. The aromatic rings have a variety of active functional groups comprising: hydroxyl, carboxylic group, phenolic group, phenolic hydroxyl, quinonyl, quinonyl and hydroxyl, alcoholic hydroxyl, sulfonic group, amino group, free quinonyl, semiquinone, quinonic oxygen group, monomethyl, and at least one kind monomethyl-active functional group which comprises methoxyl, carboxymethyl, hydroxymethyl, phenolic methyl and methylamino group.

Contents of main functional groups in the multiple-structural polyphenolic compounds are as follows: total acidic group 8.00~12.00 mg equivalent per gram, hydroxyl group 4.00~6.00 mg equivalent per gram, phenolic hydroxyl 1.00~4.00 mg equivalent per gram.

The multiple-structural polyphenolic compounds further comprise ribonucleic acid, inositol, creatinine, water-soluble glycoprotein, multi-amino acids, wood polysaccharose and multi-vitamins.

Weight percentage of the ribonucleic acid is 3~8%, total weight percentage of the inositol and the creatinine is 5~10%, total weight percentage of the water-soluble glycoprotein and the multi-amino acids is 5~10%, weight percentage of the wood polysaccharose is 8~15% and weight percentage of the multi-vitamins is 3~8%.

The multivalent phenolic hydroxyl carboxylic acid selenium complex salts are complex salts formed by the polyphenolic compounds, one or more kinds of alkali metal and selenium element, and are a new kind of organic selenium composition.

Example 1

A method for preparing selenium compounds comprises following steps of:

a) adding 2.0% urea into lignosulfonate-water solution containing 20% solid formation for serving as growth medium (pH=6.0), wherein the lignosulfonate-water solution is extracted from depickling paper pulp by sulphuric acid; and inoculating the growth medium with 2% mixed strains comprising: candida tropicalis, pseudomonas, candida utilis and strains of effective microorganisms from Japan, and fermenting for 72 hours under a temperature of 30° C. to obtain the multiple-structural polyphenolic compounds, wherein an inoculation ratio thereof is 1:2:2:2;

b) reacting the multiple-structural polyphenolic compounds with sodium hydroxide to obtain multivalent phenolic hydroxyl sodium carboxylate, wherein multiple-structual polyphenolic compounds: sodium hydroxide=1:0.5, wherein a reaction temperature thereof is 80° C., and materials are mechanically stirred to be uniformly mixed while reacting; and c) reacting the multivalent phenolic hydroxyl sodium carboxylate with $SeO_2$ to obtain multivalent phenolic hydroxyl carboxylic acid selenium complex salts, wherein the multivalent phenolic hydroxyl carboxylic acid selenium complex salts are organic selenium composition, multiple-structural polyphenolic compounds: $SeO_2$=1:0.1, a reaction temperature thereof is 80° C., and materials are mechanically stirred to be uniformly mixed while reacting.

In this example, yield of the multivalent phenolic hydroxyl carboxylic acid selenium complex salts is 51.3%.

Example 2

A method for preparing selenium compounds comprises following steps of:

a) adding 2.0% urea into lignosulfonate-water solution containing 20% solid formation for serving as growth medium (pH=6.0), wherein the lignosulfonate-water solution is extracted from depickling paper pulp by sulphuric acid; and inoculating the growth medium with 2% mixed strains comprising: candida tropicalis, pseudomonas, candida utilis and strains of effective microorganisms from Japan, and fermenting for 72 hours under a temperature of 30° C. to obtain the multiple-structural polyphenolic compounds, wherein an inoculation ratio thereof is 1:2:2:2;

b) reacting the multiple-structural polyphenolic compounds with potassium hydroxide to obtain multivalent phenolic hydroxyl potassium carboxylate, wherein multiple-structural polyphenolic compounds: potassium hydroxide=1:0.5, wherein a reaction temperature thereof is 120° C., and materials are mechanically stirred to be uniformly mixed while reacting; and c) reacting the multivalent phenolic hydroxyl potassium carboxylate with $SeO_2$ to obtain multivalent phenolic hydroxyl carboxylic acid selenium complex salts, wherein the multivalent phenolic hydroxyl carboxylic acid selenium complex salts are organic selenium composition, multiple-structural polyphenolic compounds: $SeO_2$=1:0.1, a reaction temperature thereof is 160° C., and materials are mechanically stirred to be uniformly mixed while reacting.

In this example, yield of the multivalent phenolic hydroxyl carboxylic acid selenium complex salts is 55.6%.

Example 3

A method for preparing selenium compounds comprises following steps of:

a) adding 2.0% urea into lignosulfonate-water solution containing 20% solid formation for serving as growth medium (pH=6.0), wherein the lignosulfonate-water solution is extracted from depickling paper pulp by sulphuric acid; and inoculating the growth medium with 2% mixed strains comprising: candida tropicalis, pseudomonas, candida utilis and strains of effective microorganisms from Japan, and fermenting for 72 hours under a temperature of 30° C. to obtain the multiple-structural polyphenolic compounds, wherein an inoculation ratio thereof is 1:2:2:2;

b) reacting the multiple-structural polyphenolic compounds with magnesium hydroxide to obtain multivalent phenolic hydroxyl magnesium carboxylate, wherein multiple-structural polyphenolic compounds: magnesium hydroxide=1:0.5, wherein a reaction temperature thereof is 200° C., and materials are mechanically stirred to be uniformly mixed while reacting; and c) reacting the multivalent phenolic hydroxyl magnesium carboxylate with $SeO_2$ to obtain multivalent phenolic hydroxyl carboxylic acid selenium complex salts, wherein the multivalent phenolic hydroxyl carboxylic acid selenium complex salts are organic selenium composition, multiple-structural polyphenolic compounds: $SeO_2$=1:0.1, a reaction temperature thereof is 180° C., and materials are mechanically stirred to be uniformly mixed while reacting.

In this example, yield of the multivalent phenolic hydroxyl carboxylic acid selenium complex salts is 52.1%.

One skilled in the art will understand that the embodiment of the present invention as shown in the illustrations and described above is exemplary only and not intended to be limiting.

It will thus be seen that the objects of the present invention have been fully and effectively accomplished. Its embodiments have been shown and described for the purposes of illustrating the functional and structural principles of the present invention and are subject to change without departure from such principles. Therefore, this invention includes all modifications encompassed within the spirit and scope of the following claims.

In following toxicity test, sample-1, sample-2 and sample-3 are multivalent phenolic hydroxyl carboxylate produced according to an embodiment 1, an embodiment 2 and an embodiment 3 of the present invention, respectively.

Acute Toxicity Test of Sample-1 in Mice by Intragastrical Administration

Summary

In this test, acute toxicity of the sample-1 in mice by one-time intragastrical administration is observed. Poisoning manifestations and death rate of the mice tested are observed within 14 days of poisoning. Results show that $LD_{50}$ of the sample-1 in the mice by intragastrical administration is 260 mg·kg$^{-1}$.

1 Object: observing acute toxicity reaction and death rate of the mice by intragastrical administration of the sample-1.

2 Medicine for testing and menstruum 2.1 The medicine for testing

Name: sample-1

Shape and properties: brown powder

Content: 208 mg/g

Batch number: 20120611

2.2 The menstruum: 0.5% sodium carboxymethyl cellulose (CMC)

3. Animals

Source: Kunming mice, provided by Department of Animal Science, Fudan University.

Certification number: SCXK (Shanghai) 2009-0019

Weight: 18~22 g

Sexuality: half male and half female

4. Externally environment conditions for feeding and administrating the animals 4.1 Environmental conditions: temperature: 18~22° C., humidity: 45~65%

4.2 Feeding facility: SPF laboratory animal house

5 Feed: mice feed, provided by Shanghai Shilin Biological Science and Technology Ltd. and a batch number thereof is Q/TJCX 1-2010.

6 Bedding: wood shaving, provided by Department of Animal Science, Fudan University.

7 Information about drinking water: tap water.

8 Experimental method 8.1 Designed dose rate: 4 groups are divided in this experiment, and the dose rates thereof are 490 mg/kg, 343 mg/kg, 240 mg/kg and 168 mg/kg, respectively; and a group interval thereof is 0.7.

8.2 Preparation method of the medicine for testing (the sample-1): adding 0.5% CMC (Carboxy Methylated Cellulose) to the sample-1 and grinding it, then successively diluting it to suspensions having corresponding density.

8.3 Medicine administration methods and approaches: The animals are randomly divided into 4 groups according to their sexuality, and each group has 10 mice, with half male and half female. All of the mice are fasted for 14 hours (supplying nothing but water) before experiments. Then the mice are administered intragastrically with the medicine by a dose of 20 ml/kg. Poisoning and death conditions of the animals are observed within 14 days after the medicine administration.

9 Operation, inspection and determination of the experiment 9.1 General symptoms: observing poisoning symptom of the mice in activity behaviors, fur and excreta, and observing lethality.

9.2 Weight determination: weighing the mice once before the medicine administration, one week after the beginning of the experiment and before executing the mice when the experiment is over, respectively.

9.3 Observation indexes: processing gross anatomy on animals dead during course of the experiment and animals still alive when the experiment is over, observing pathologic changes of principal organs by naked eye.

9.4 Observation period: observing the animals every 10 minutes within 4 hours after the animals are poisoned, and then observing the animals twice a day, morning and afternoon, respectively.

10 Data processing: $LD_{50}$ and 95% confidence limit are calculated by processing the data with SPSS16.0 statistical software using weighted probit regression model (Bliss method).

11 Results:

In high-dose group, spontaneous activity of the mice decreases. After about 30 minutes the mice start to lie in the prone position, coating hair thereof tarnishes, and mild diarrhea appears on part of the mice. After being poisoned for 1 hour, the mice begin to die, and the death mainly appears within 4 hours. Dying mice have a symptom of clonic convulsion. Poisoned mice return to normal in 3 days. In mid-dose and low-dose groups, toxicity reaction of the mice caused by poisoning is the same as that in the high-dose group, but the only difference lies in a delay of poisoning time. After the experiment, all of the mice gain weight to varying degrees. (See Table 1)

After processing gross anatomy on mice dead in the experiment and mice still alive when the experiment is over, no obvious pathological changes demonstrate by observing with naked eye.

Referring to Table 2 for $LD_{50}$ and 95% confidence limit of sample-1 in the mice by intragastrical administration.

TABLE 1

Effect of acute toxicity of the sample-1 by intragastrical administration on weight changes of the mice ($\bar{x} \pm s$)

| Dosage (mg · kg$^{-1}$) | 0 d | 7 d | 14 d |
|---|---|---|---|
| 490 | | | |
| 343 | | | |
| 240 | | | |
| 168 | | | |

TABLE 2

$LD_{50}$ and 95% confidence limit of sample-1 in mice by intragastrical administration

| Dosage (mg · kg$^{-1}$) | Dosage Logarithm | Animal count | Death count | Death rate (%) | $LD_{50}$ and 95% confidence limit |
|---|---|---|---|---|---|
| 490 | 2.690 | 10 | 9 | 90 | $LD_{50}$ = 260 mg · kg$^{-1}$, 95% confidence limit is 167~357 mg · kg$^{-1}$ |
| 343 | 2.535 | 10 | 6 | 60 | |
| 240 | 2.380 | 10 | 4 | 40 | |
| 168 | 2.225 | 10 | 3 | 30 | |

12 Conclusion $LD_{50}$ of the sample-1 is 260 mg/kg, and 95% confidence limit thereof is 167~357 mg/kg.

References

1. Guiding principle for investigative techniques of acute toxicity of chemical medicine, guiding principle number [H] GPT 1-1
2. General principle for non-clinical safety technical evaluation of therapeutic biologics, guiding principle number [S] GTP 1-1

Acute Toxicity Test of Sample-2 in Mice by Intragastrical Administration

Summary

In this test, acute toxicity of sample-2 in mice by one-time intragastrical administration is observed. Poisoning manifestations and death rate of the mice tested are observed within 14 days of poisoning. Results show that $LD_{50}$ of the sample-2 in the mice by intragastrical administration is 328 mg·kg$^{-1}$.

1 Object: observing acute toxicity reaction and death rate of the mice by intragasrical administration of the sample-2.

2 Medicine for testing and menstruum 2.1 The medicine for testing

Name: sample-2

Shape and properties: brown powder

Content: 208 mg/g

Batch number: 20120618

2.2 The menstruum: 0.5% sodium carboxymethyl cellulose (CMC)

3. Animals

Source: Kunming mice, provided by Department of Animal Science, Fudan University.

Certification number: SCXK(Shanghai) 2009-0019

Weight: 18~22 g

Sexuality: half male and half female

4. Externally environmental conditions for feeding and administrating the animals 4.1 Environmental conditions: temperature: 18~22° C., humidity: 45~65%

4.2 Feeding facility: SPF laboratory animal house

5 Feed: mice feed, provided by Shanghai Shilin Biological Science and Technology Ltd. and a batch number thereof is Q/TJCX 1-2010.

6 Bedding: wood shaving, provided by Department of Animal Science, Fudan University.

7 Information about drinking water: tap water.

8 Experimental method 8.1 Designed dose rate: 5 groups are divided in this experiment, and the dose rates thereof are 600 mg/kg, 450 mg/kg, 338 mg/kg, 253 mg/kg and 190 mg/kg, respectively; and a group interval thereof is 0.75.

8.2 Preparation method of the medicine for testing (the sample-2): adding 0.5% CMC (Carboxy Methylated Cellulose) to the sample-2 and grinding it, then successively diluting it to suspensions having corresponding density.

8.3 Medicine administration methods and approaches: The animals are randomly divided into 5 groups according to sexuality, and each group has 10 mice, with half male and half female. All of the mice are fasted for 14 hours (supplying nothing but water) before experiments. Then the mice are administered intragastrically with the medicine by a dose of 20 ml/kg. Poisoning and death conditions of the animals are observed within 14 days after the medicine administration.

9 Operation, inspection and determination of the experiment 9.1 General symptoms: observing poisoning symptom of the mice in activity behaviors, fur and excreta, and observing lethality.

9.2 Weight determination: weighing the mice once before the medicine administration, one week after the beginning of the experiment and before executing the mice when the experiment is over, respectively.

9.3 Observation indexes: processing gross anatomy on animals dead during the course of the experiment and animals still alive when the experiment is over, observing pathologic changes of principal organs by naked eye.

9.4 Observation period: observing the animals every 10 minutes within 4 hours after the animals are poisoned, and then observing the animals twice a day, morning and afternoon, respectively.

10 Data processing: $LD_{50}$ and 95% confidence limit are calculated by processing the data with SPSS16.0 statistical software using weighted probit regression model (Bliss method).

11 Results: In high-dose group, spontaneous activity of the mice decreases. After about 15 minutes the mice start to lie in the prone position, coating hair thereof tarnishes, and mild diarrhoea appears on part of the mice. After being poisoned for 30 minutes, the mice begin to die, and the death mainly appears in 4 hours. Dying mice have a symptom of clonic convulsion. Poisoned mice return to normal in 3 days. In mid-dose and low-dose groups, toxicity reaction of the mice caused by poisoning is the same as that in the high-dose group, but the only difference lies in a delay of poisoning time. After the experiment, all of the mice gain weight to varying degrees. (See Table 1)

After processing gross anatomy on mice dead in the experiment and mice still alive when the experiment is over, no obvious pathological changes demonstrate by observing with naked eye.

Referring to Table 2 for $LD_{50}$ and 95% confidence limit of sample-2 in the mice by intragastrical administration.

TABLE 1

Effect of acute toxicity of the sample-2 by intragastrical administration on weight changes of the mice ($\bar{x} \pm s$)

| Dosage (mg · kg$^{-1}$) | 0 d | 7 d | 14 d |
|---|---|---|---|
| 600 | | | |
| 450 | | | |
| 338 | | | |
| 253 | | | |
| 190 | | | |

TABLE 2

$LD_{50}$ and 95% confidence limit of sample-2 in mice by intragastrical administration

| Dosage (mg · kg$^{-1}$) | Dosage Logarithm | Animal count | Death count | Death rate (%) | $LD_{50}$ and 95% confidence limit |
|---|---|---|---|---|---|
| 600 | 2.778 | 10 | 9 | 90 | $LD_{50}$ = 328 mg · kg$^{-1}$ |
| 450 | 2.653 | 10 | 7 | 70 | 95% confidence |
| 338 | 2.529 | 10 | 6 | 60 | limit is |
| 253 | 2.403 | 10 | 3 | 30 | 262~404 mg · kg$^{-1}$ |
| 190 | 2.225 | 10 | 1 | 10 | |

12 Conclusion $LD_{50}$ of the sample-2 is 328 mg/kg, and 95% confidence limit thereof is 262~404 mg/kg.

References

1. Guiding principle for investigative techniques of acute toxicity of chemical medicine, guiding principle number [H] GPT 1-1
2. General principle for non-clinical safety technical evaluation of therapeutic biologics, guiding principle number [S] GTP 1-1

Acute Toxicity Test of Sample-3 in Mice by Intragastrical Administration

Summary

In this test, acute toxicity of the sample-3 in mice by one-time intragastrical administration is observed. Poisoning manifestations and death rate of the mice tested are observed within 14 days of poisoning. Results show that $LD_{50}$ of the sample-3 in the mice by intragastrical administration is 177 mg·kg$^{-1}$.

1 Object: observing acute toxicity reaction and death rate of the mice by intragastrical administration of the sample-3.

2 Medicine for testing and menstruum 2.1 The medicine for testing

Name: sample-3

Shape and properties: brown powder

Content: 104 mg/g

Batch number: 20120618

2.2 The menstruum: 0.5% sodium carboxymethyl cellulose (CMC)

3. Animals

Source: Kunming mice, provided by Department of Animal Science, Fudan University.

Certification number: SCXK (Shanghai) 2009-0019

Weight: 18~22 g

Sexuality: half male and half female

4. Externally environmental conditions for feeding and administrating the animals 4.1 Environmental conditions: temperature: 18~22° C., humidity: 45~65%

4.2 Feeding facility: SPF laboratory animal house

5 Feed: mice feed, provided by Shanghai Shilin Biological Science and Technology Ltd. and a batch number thereof is Q/TJCX 1-2010.

6 Bedding: wood shaving, provided by Department of Animal Science, Fudan University.

7 Information about drinking water: tap water.

8 Experimental method 8.1 Designed dose rate: 4 groups are divided in this experiment, and the dose rates thereof are 253 mg/kg, 189 mg/kg, 142 mg/kg and 107 mg/kg, respectively; and a group interval thereof is 0.75.

8.2 Preparation method of the medicine for testing (the sample-3): adding 0.5% CMC (Carboxy Methylated Cellulose) to the sample-3 and grinding it, and then successively diluting it to suspensions having corresponding density.

8.3 Medicine administration methods and approaches: The animals are randomly divided into 4 groups according to their sexuality, and each group has 10 mice, with half male and half female. All of the mice are fasted for 14 hours (supplying nothing but water) before experiments. Then the mice are administered intragastrically with the medicine by a dose of 20 ml/kg. Poisoning and death conditions of the animals are observed within 14 days after the medicine administration.

9 Operation, inspection and determination of the experiment 9.1 General symptoms: observing poisoning symptom of the mice in activity behaviors, fur and excreta, and observing lethality.

9.2 Weight determination: weighing the mice once before the medicine administration, one week after the beginning of the experiment and before executing the mice when the experiment is over, respectively.

9.3 Observation indexes: processing gross anatomy on animals dead during the course of the experiment and animals still alive when the experiment is over, observing pathologic changes of principal organs by naked eye.

9.4 Observation period: observing the animals every 10 minutes within 4 hours after the animals are poisoned, and then observing the animals twice a day, morning and afternoon, respectively.

10 Data processing: $LD_{50}$ and 95% confidence limit are calculated by processing the data with SPSS16.0 statistical software using weighted probit regression model (Bliss method).

11 Results: In high-dose group, spontaneous activity of the mice decreases. After about 30 minutes the mice start to lie in the prone position, coating hair thereof tarnishes, and mild diarrhea appears on part of the mice. After being poisoned for 1 hour, the mice begin to die, and the death mainly appears in 4 hours. Dying mice have a symptom of clonic convulsion. Poisoned mice return to normal in 3 days. In mid-dose and low-dose groups, toxicity reaction of the mice caused by poisoning is the same as that in the high-dose group, but the only difference lies in a delay of poisoning time. After the experiment, all of the mice gain weight to varying degrees. (See Table 1)

After processing gross anatomy on mice dead in the experiment and mice still alive when the experiment is over, no obvious pathological changes demonstrate by observing with naked eye.

Referring to Table 2 for $LD_{50}$ and 95% confidence limit of sample-3 in the mice by intragastrical administration.

TABLE 1

Effect of acute toxicity of the sample-3 by intragastrical administration on weight changes of the mice ($\bar{x} \pm s$)

| Dosage (mg · kg$^{-1}$) | 0 d | 7 d | 14 d |
|---|---|---|---|
| 253 | | | |
| 189 | | | |
| 142 | | | |
| 107 | | | |

TABLE 2

$LD_{50}$ and 95% confidence limit of sample-3 in mice by intragastrical administration

| Dosage (mg · kg$^{-1}$) | Dosage Logarithm | Animal count | Death count | Death rate (%) | $LD_{50}$ and 95% confidence limit |
|---|---|---|---|---|---|
| 253 | 2.403 | 10 | 8 | 80 | $LD_{50}$ = 177 mg · kg$^{-1}$ |
| 189 | 2.276 | 10 | 5 | 50 | 95% confidence |
| 142 | 2.152 | 10 | 3 | 30 | limit is |
| 107 | 2.029 | 10 | 2 | 20 | 137~256 mg · kg$^{-1}$ |

12 Conclusion $LD_{50}$ of the sample-3 is 177 mg/kg, and 95% confidence limit thereof is 137~256 mg/kg.

References
1. Guiding principle for investigative techniques of acute toxicity of chemical medicine, guiding principle number [H] GPT 1-1
2. General principle for non-clinical safety technical evaluation of therapeutic biologics, guiding principle number [S] GTP 1-1

According to an amount of an average $LD_{50}$ reported in the three acute toxicity tests of the mice mentioned above, if the organic selenium composition is applied to a 60-kilogram human body, a dosage of over 200000 μg per day is taken and no toxicity and side effects will be found. The dosage are 500~1000 times of a dosage per day restricted by countries of the world (including China).

What is claimed is:

1. A method for preparing selenium compounds, comprising following steps of:
   A. hydrolyzing lignin to obtain multiple-structural polyphenolic compounds, wherein the multiple-structural polyphenolic compounds are slightly acid, and a pH value thereof is 4.5~6.5, the multiple-structural polyphenolic compounds have good water solubility, an average molecular weight thereof is 200~500, and elemental compositions thereof are as follows: C: 38.00-44.00%, H: 2.20-4.29%, O: 40.00-45.00%, N: 2.00-4.00%, S: 3.00-5.00%;
   molecules of the multiple-structural polyphenolic compounds have aromatic rings or other heterocycles comprising pyrrole, furan and indole, the aromatic rings are connected by bridge bond, the aromatic rings have a variety of active functional groups comprising: hydroxyl, carboxylic group, phenolic group, phenolic hydroxyl, quinonyl, quinonyl and hydroxyl, alcoholic hydroxyl, sulfonic group, amino group, free quinonyl, semiquinone, quinonic oxygen group, monomethyl, and at least one kind monomethyl-active functional group which comprises methoxyl, carboxymethyl, hydroxymethyl, phenolic methyl and methylamino group;
   contents of main functional groups in the multiple-structural polyphenolic compounds are as follows: total acidic group 8.00~12.00 mg equivalent per gram, hydroxyl group 4.00~6.00 mg equivalent per gram, phenolic hydroxyl 1.00~4.00 mg equivalent per gram;
   the multiple-structural polyphenolic compounds further comprise ribonucleic acid, inositol, creatinine, water-soluble glycoprotein, multi-amino acids, wood polysaccharose and multi-vitamins;
   weight percentage of the ribonucleic acid is 3~8%, total weight percentage of the inositol and the creatinine is 5~10%, total weight percentage of the water-soluble glycoprotein and the multi-amino acids is 5~10%, weight percentage of the wood polysaccharose is 8~15% and weight percentage of the multi-vitamins is 3~8%;

B. reacting the multiple-structural polyphenolic compounds with at least one kind of inorganic metal base to obtain multivalent phenolic hydroxyl carboxylate; and C. reacting the multivalent phenolic hydroxyl carboxylate with $SeO_2$ to obtain multivalent phenolic hydroxyl carboxylic acid selenium complex salts, wherein the multivalent phenolic hydroxyl carboxylic acid selenium complex salts are organic selenium composition, the multivalent phenolic hydroxyl carboxylic acid selenium complex salts comprises:

2. The method for preparing the selenium compounds, as recited in claim 1, wherein a material rate in the step B is: multiple-structural polyphenolic compounds: inorganic and metal base is 1:0.1~0.8, wherein a reaction temperature thereof is 80° C.~200° C., and materials are mechanically stirred to be uniformly mixed while reacting.

3. The method for preparing the selenium compounds, as recited in claim 1, wherein a material ratio in the step C is: multiple-structural polyphenolic compounds: $SeO_2$=1: 0.03~0.5, wherein a reaction temperature thereof is 80° C.~180° C., and materials are mechanically stirred to be uniformly mixed while reacting.

4. The method for preparing the selenium compounds, as recited in claim 1, wherein specific process of the step A comprises following steps of:

adding 0.5~4.0% urea into lignosulfonate-water solution having 5~30% solid formation for serving as growth medium (pH=4.5~6.5), wherein the lignosulfonate-water solution is extracted from depickling paper pulp by sulphuric acid; and inoculating the growth medium with 0.5~10% mixed strains comprising: *candida tropicalis, pseudomonas, candida utilis* and strains of effective microorganisms from Japan and fermenting it to obtain the multiple-structural polyphenolic compounds, wherein a fermentation temperature thereof is 20~40° C.

5. The method for preparing the selenium compounds, as recited in claim 1, wherein the inorganic and metal base are selected from the group consisting of potassium hydroxide, sodium hydroxide, calcium hydroxide, magnesium hydroxide, manganese hydroxide, lithium hydroxide and zinc hydroxide.

6. The method for preparing the selenium compounds, as recited in claim 1, wherein the multivalent phenolic hydroxyl carboxylate comprises:

wherein $R^+$ is at least one kind of alkali metal ion.

7. A multivalent phenolic hydroxyl carboxylic acid selenium complex salts product produced according to the method for preparing the selenium compounds of claim 1.

8. The multivalent phenolic hydroxyl carboxylic acid selenium complex salts produced according to the method for preparing the selenium compounds, as recited in claim 1, having a high performance liquid chromatography diagram with characteristic peaks 1, 2, 3 and 23 shown in FIG. 2 of the illustrations.

9. A method for preparing selenium compounds, comprising steps of:

a) adding 2.0% urea into lignosulfonate-water solution containing 20% solid formation for serving as growth medium (pH=6.0), wherein the lignosulfonate-water solution is extracted from depickling paper pulp by sulphuric acid; and inoculating the growth medium with 2% mixed strains comprising: *candida tropicalis, pseudomonas, candida utilis* and strains of effective microorganisms from Japan, and fermenting for 72 hours under a temperature of 30° C. to obtain the multiple-structural polyphenolic compounds, wherein an inoculation ratio thereof is 1:2:2:2, wherein the multiple-structural polyphenolic compounds are slightly acid, and a pH value thereof is 4.5~6.5, the multiple-structural polyphenolic compounds have good water solubility, an average molecular weight thereof is 200~500, and elemental compositions thereof are as follows: C: 38.00-44.00%, H: 2.20-4.29%, O: 40.00-45.00%, N: 2.00-4.00%, S: 3.00-5.00%;

molecules of the multiple-structural polyphenolic compounds have aromatic rings or other heterocycles comprising pyrrole, furan and indole, the aromatic rings are connected by bridge bond, the aromatic rings have a variety of active functional groups comprising: hydroxyl, carboxylic group, phenolic group, phenolic hydroxyl, quinonyl, quinonyl and hydroxyl, alcoholic hydroxyl, sulfonic group, amino group, free quinonyl, semiquinone, quinonic oxygen group, monomethyl, and at least one kind monomethyl-active functional group which comprises methoxyl, carboxymethyl, hydroxymethyl, phenolic methyl and methylamino group;

contents of main functional groups in the multiple-structural polyphenolic compounds are as follows: total acidic group 8.00~12.00 mg equivalent per gram, hydroxyl group 4.00~6.00 mg equivalent per gram, phenolic hydroxyl 1.00~4.00 mg equivalent per gram;

the multiple-structural polyphenolic compounds further comprise ribonucleic acid, inositol, creatinine, water-soluble glycoprotein, multi-amino acids, wood polysaccharose and multi-vitamins;

weight percentage of the ribonucleic acid is 3~8%, total weight percentage of the inositol and the creatinine is 5~10%, total weight percentage of the water-soluble glycoprotein and the multi-amino acids is 5~10%, weight percentage of the wood polysaccharose is 8~15% and weight percentage of the multi-vitamins is 3~8%;

b) reacting the multiple-structural polyphenolic compounds with sodium hydroxide to obtain multivalent phenolic hydroxyl sodium carboxylate, wherein multiple-structural polyphenolic compounds: sodium hydroxide=1:0.5, wherein a reaction temperature thereof is 80° C., and materials are mechanically stirred to be uniformly mixed while reacting; and c) reacting the multivalent phenolic hydroxyl sodium carboxylate with $SeO_2$ to obtain multivalent phenolic hydroxyl carboxylic acid selenium complex salts, wherein the multivalent phenolic hydroxyl carboxylic acid selenium complex salts are organic selenium composition, multiple-structural polyphenolic compounds: $SeO_2$=1:0.1, a reaction temperature thereof is 80° C., and materials are mechanically stirred to be uniformly mixed while reacting; wherein the multivalent phenolic hydroxyl carboxylic acid selenium complex salts comprises:

* * * * *